United States Patent
Hostettler et al.

(10) Patent No.: US 6,290,679 B1
(45) Date of Patent: Sep. 18, 2001

(54) DEVICE FOR METERED ADMINISTRATION OF AN INJECTABLE PRODUCT

(75) Inventors: Peter Hostettler, Ersigen; Hanspeter Heiniger, Lotzwil, both of (CH)

(73) Assignee: Disetronic Licensing AG, Burgdorf (CH)

(*) Notice: Subject to any disclaimer, the term of this patent is extended or adjusted under 35 U.S.C. 154(b) by 0 days.

(21) Appl. No.: 09/311,438

(22) Filed: May 14, 1999

(51) Int. Cl.$^7$ ............................................. A61M 5/00
(52) U.S. Cl. ................................................. 604/208
(58) Field of Search ........................... 604/136, 191, 604/195, 196, 207, 208, 218, 223, 226, 232, 233

(56) References Cited

U.S. PATENT DOCUMENTS

| | | |
|---|---|---|
| 4,592,745 * | 6/1986 | Rex et al. .............................. 604/211 |
| 4,865,591 | 9/1989 | Sams . |
| 4,883,472 | 11/1989 | Michel . |
| 4,946,446 | 8/1990 | Vadher . |
| 4,973,318 | 11/1990 | Holm et al. . |
| 5,017,190 | 5/1991 | Simon et al. . |
| 5,084,060 | 1/1992 | Freund et al. . |
| 5,114,406 | 5/1992 | Gabriel et al. . |
| 5,273,544 | 12/1993 | van der Waal . |
| 5,279,579 | 1/1994 | D'Amico . |
| 5,279,585 | 1/1994 | Balkwill . |
| 5,292,314 | 3/1994 | D'Alessio et al. . |
| 5,295,976 | 3/1994 | Harris . |
| 5,320,609 | 6/1994 | Haber et al. . |
| 5,336,183 | 8/1994 | Greelis et al. . |
| 5,338,311 | 8/1994 | Mahukar . |
| 5,370,629 | 12/1994 | Michel et al. . |
| 5,472,430 | 12/1995 | Vaillancourt et al. . |
| 5,496,293 | 3/1996 | Huggenberger . |
| 5,514,097 | 5/1996 | Knauer . |
| 5,527,294 | 6/1996 | Weatherford et al. . |
| 5,540,664 * | 7/1996 | Wyrick ................................. 604/136 |
| 5,549,558 | 8/1996 | Martin . |
| 5,549,575 | 8/1996 | Giambattista et al. . |
| 5,573,510 | 11/1996 | Issacson . |
| 5,582,598 | 12/1996 | Chanoch . |
| 5,591,136 | 1/1997 | Gabriel . |
| 5,591,138 | 1/1997 | Vaillancourt . |
| 5,593,390 | 1/1997 | Castellano et al. . |
| 5,609,577 | 3/1997 | Haber et al. . |
| 5,643,214 | 7/1997 | Marshall et al. . |
| 5,658,259 | 8/1997 | Pearson et al. . |
| 5,674,204 | 10/1997 | Chanoch . |
| 5,679,111 | 10/1997 | Hjertman et al. . |
| 5,725,508 | 3/1998 | Chanoch et al. . |
| 5,728,074 | 3/1998 | Castellano et al. . |
| 5,743,889 | 4/1998 | Sams . |
| 5,807,346 | 9/1998 | Frezza . |

FOREIGN PATENT DOCUMENTS

| | | |
|---|---|---|
| 3638984 | 11/1986 | (DE) . |
| 3645245 | 11/1986 | (DE) . |
| 3900926 | 8/1989 | (DE) . |
| 4223958 | 7/1992 | (DE) . |
| 0037696 | 3/1981 | (EP) . |
| 0058536 | 8/1982 | (EP) . |
| 0245312 | 10/1986 | (EP) . |
| 0268191 | 11/1987 | (EP) . |
| 0298067 | 6/1988 | (EP) . |
| 327910 | 1/1989 | (EP) . |
| 0373321 | 6/1990 | (EP) . |
| 496141 | 1/1991 | (EP) . |
| 0516473 | 5/1992 | (EP) . |
| 0498737 | 8/1992 | (EP) . |
| 0554995 | 8/1993 | (EP) . |
| 0594349 | 4/1994 | (EP) . |
| 0627229 | 5/1994 | (EP) . |
| 2701211 | 8/1994 | (FR) . |
| WO 8702895 | 5/1987 | (WO) . |
| WO 9110460 | 7/1991 | (WO) . |
| WO 9305835 | 8/1992 | (WO) . |
| WO 9218179 | 10/1992 | (WO) . |
| WO 9316740 | 9/1993 | (WO) . |
| WO 9409841 | 5/1994 | (WO) . |
| WO 9415120 | 7/1994 | (WO) . |
| WO 9501812 | 1/1995 | (WO) . |
| WO 9504563 | 2/1995 | (WO) . |
| WO 9607443 | 3/1996 | (WO) . |

* cited by examiner

Primary Examiner—Anhtuan T. Nguyen
Assistant Examiner—Ann Y. Lam
(74) Attorney, Agent, or Firm—Dorsey & Whitney LLP

(57) ABSTRACT

The present invention provides a device for metered administration of an injectable product including a base section, a container, a drive unit including a driven member projecting into the container, and a metering device for setting the path length of displacement of the driven member in relation to the base section upon actuation of the drive unit, wherein the metering device includes a first and second metering structure.

16 Claims, 4 Drawing Sheets

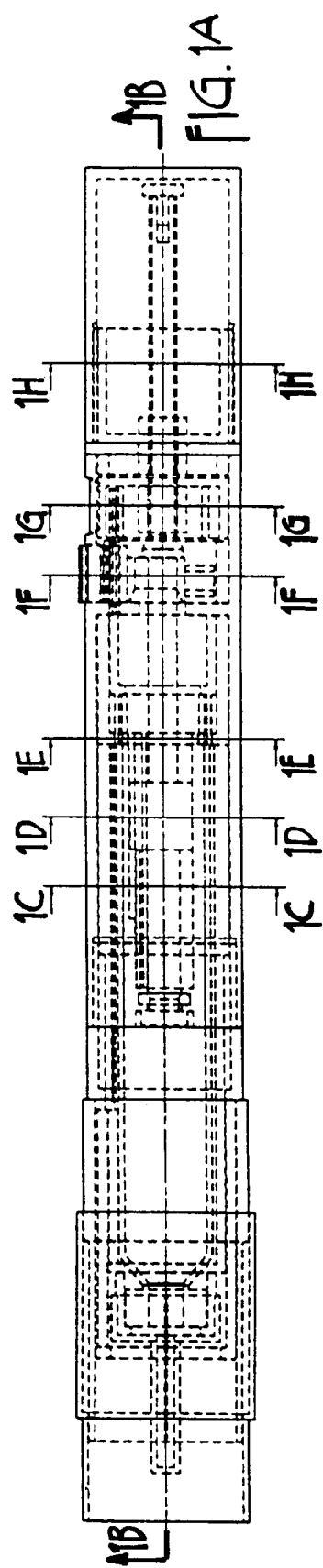
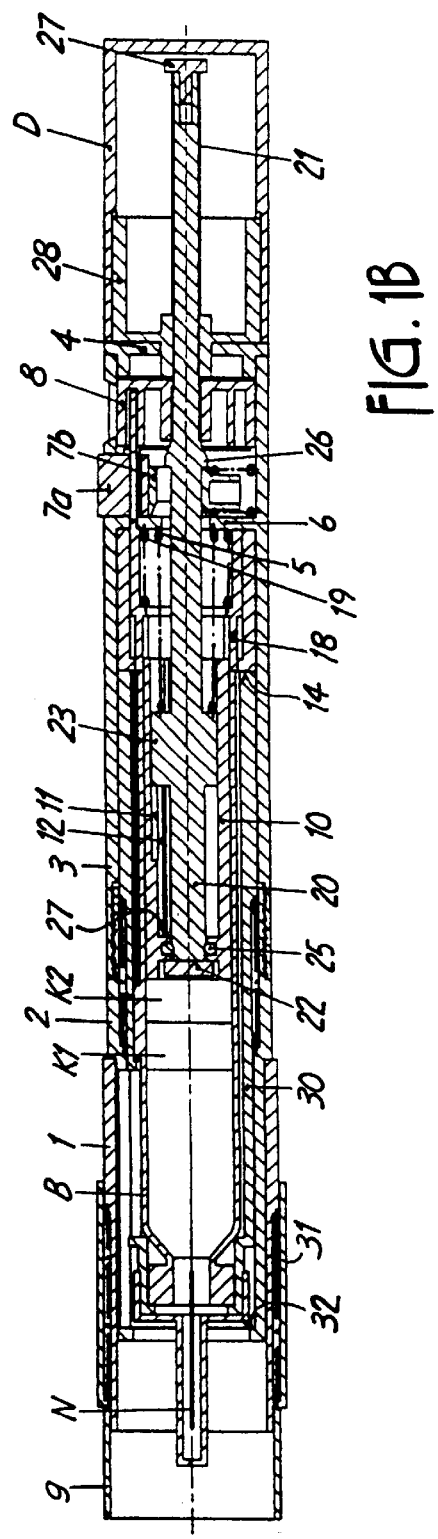
FIG. 1A
FIG. 1B

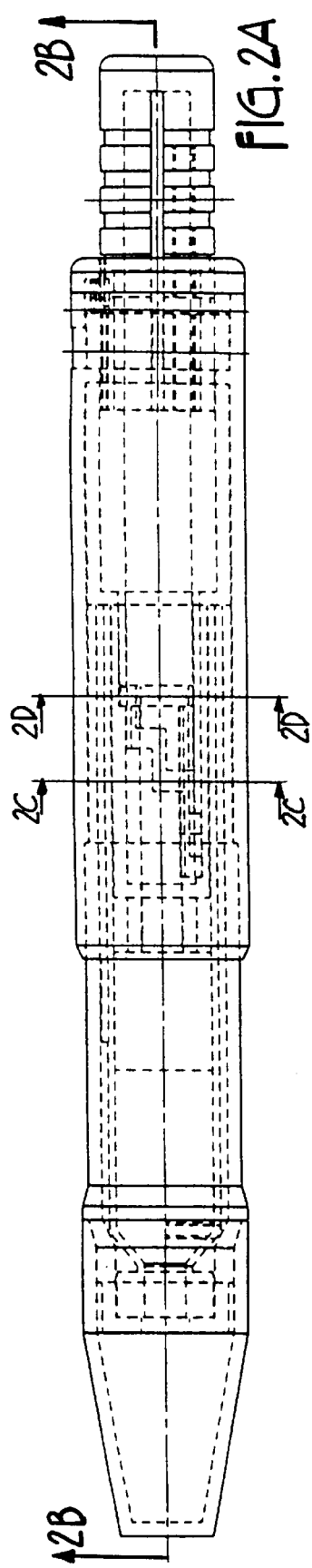
FIG. 2A
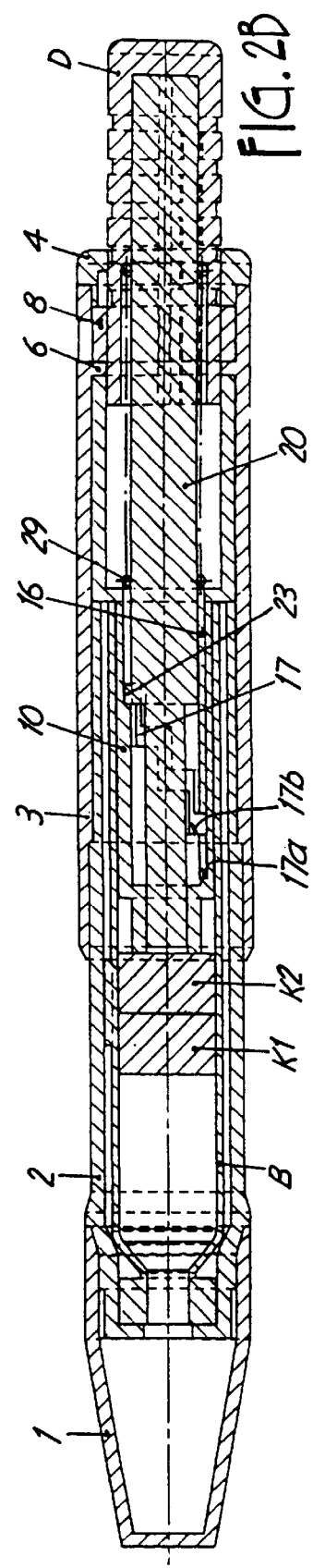
FIG. 2B
FIG. 2D
FIG. 2C

DEVICE FOR METERED ADMINISTRATION OF AN INJECTABLE PRODUCT

RELATED APPLICATIONS

This applications claims the priority of German Patent Application No. 198 21 934.3 filed May 15, 1998, which is incorporated herein by reference.

BACKGROUND

The invention relates to injection devices and, more particularly, to an injection device for providing for the metered administration of an injectable product.

EP 0 298 067 B1 discloses an injection pen comprising a dual chamber ampoule (or ampule). The pen comprises a base section, a container accommodated by said base section, a drive unit and a metering device. A product dose is dispensed from the container through a needle by advancing in forward direction a piston arranged in said container. The drive unit comprises a driven member projecting into the container, displacing the piston in forward direction upon actuation of the drive unit. The length of the stroke, by which the driven member is displaced in forward direction of the piston in relation to the base section upon actuation of the drive mechanism, is set by means of the metering device. The base section is an enclosure surrounding the container, the drive unit and the metering device. The device, and others generally similar to it, is used for injection or infusion of a generally liquid drug solution.

SUMMARY

It is an object of the present invention to provide an injection device for metered administration of an injectable product, such as a liquid drug solution, in particular a medical or cosmetic drug solution such as insulin, wherein the device is configured as simply as possible and is as short in length as possible.

In one embodiment, the present invention provides a device for metered administration of an injectable product including a base section, a container, a drive unit including a driven member projecting into the container, and a metering device for setting the path length of displacement of the driven member in relation to the base section upon actuation of the drive unit, wherein the metering device includes a first and second metering structure arranged in the container, the second being adjustable in relation to the first, and wherein metering is effected by interaction of the first and second metering structures.

In one embodiment, the present invention provides a device comprising a base section, a container accommodated by said base section, a drive unit and a metering device. A product dose is dispensed from the container through a needle by advancing in forward direction at least one piston arranged in said container. The drive unit comprises a driven member projecting into the container, which displaces the piston in forward direction upon actuation of the drive unit. The length of the stroke, by which the driven member is displaced in forward or dispensing direction of the piston in relation to the base section upon actuation of the drive mechanism, is set by means of the metering device.

The base section is preferably an enclosure substantially, but not necessarily, surrounding the container, the drive unit and the metering device. The device is used for injection or infusion of a generally liquid drug solution, preferably a medical or cosmetic liquid. In particular and preferably, the invention refers to a portable device, a so-called injection pen.

According to the invention, at least a first metering means and at least a second metering means, the second one being adjustable in relation to the first, are provided in the container, and metering is effected by interaction of the first and second metering means within the container.

According to the invention, the space of the container located behind the piston, when looked at in forward direction, is used for accommodating the metering means of the metering device. The overall length may be shortened by providing a container that projects at least somewhat over the piston at the rear. This is particularly the case in multi-chamber ampoules in which several in-line chambers are separated from each other by pistons and are closed by a rear piston. Owing to the fact that generally the rear piston is pushed against the front piston(s) for mixing the chamber contents prior to the first injection, a free rear container space is compulsorily or customarily generated.

In a preferred embodiment of the present invention, i.e. in a device comprising said multi-chamber ampoule, the free container space is used for arranging the metering means of the metering device, preferably the complete metering device. In addition, a reduction in components is achieved if the mixing member known per se in such devices, mixing being accomplished according to the prior art by driving the rear piston forward for mixing the chamber contents, is simultaneously formed as a carrier of at least one metering means, thus becoming a component of the metering device.

In a preferred embodiment of the invention, the first metering means is provided at such a mixing member, and the second metering means is directly provided at the driven member. In this embodiment, metering is directly effected between the two components of the device moved in relation to each other for advancing the piston. The mixing member may be configured as a mixing rod and in this design would be surrounded by the driven member, designed as a driven sleeve. Preferably, however, the mixing member is designed as a mixing sleeve and/or a mixing tube, and surrounds the driven member, thus obtaining the structure of both the drive unit and the metering device.

The metering device is preferably arranged between two components of the metering device projecting into the container, similar to a coulisse guiding.

In one embodiment, the coulisse or link guide system is preferably formed by a recess within the area of an internal circumferential face of the sleeve component and an engaging cam. The recess comprises the first metering means, and the cam the second. In a preferred embodiment, the recess forms a guide channel for the cam.

The components of the metering device, at which the first metering means is formed, may be simply produced in that the recess may be generated by joining several cylindrical bodies, wherein at least one of these bodies is a hollow cylinder or bowl-shaped, respectively. Preferably both bodies are designed as sleeve bodies or bowl-shaped bodies.

A stepped recess is obtained by two cylindrical bodies comprising stepped front faces. Two bowl-shaped bodies may be inserted in-line in forward direction in a third sleeve body, thus forming the stepped recess between them.

Metering by means of an adjusting spindle, however, could also be provided. The spindle drive for metering would be formed by the component comprising the first metering means plus an additional adjusting sleeve, simultaneously acting as a straight guide for the driven member. Said metering mechanisms are known per se in injection pens, but prior to the present invention, they have not been located or arranged within a container of an injection pen.

In one embodiment of the invention, the component of the metering device, at which the first metering means is formed, preferably a mixing member, may be used simultaneously as a transfer member, transferring a forward movement of the driven member to the container. This dual function is applied in so-called auto-injection devices, in which the container is displaced into a frontal position in relation to the base section for inserting the hypodermic needle which is usually firmly attached to the container.

Other objects, features, embodiments and advantages of the device and method of the present invention will become more fully apparent and understood with reference to the following description and appended drawings and claims.

BRIEF DESCRIPTION OF THE DRAWINGS

FIGS. 1a–i includes an elevational view, an elevational cross-sectional view and a number of cross-sectional views, and depicts an auto-injection device for dual dispensing;

FIGS. 2a–d includes an elevational view, an elevational cross-sectional view and two cross-sectional views, and depicts an injection device for dispensing a drug four times.

DETAILED DESCRIPTION

Figure 1C:
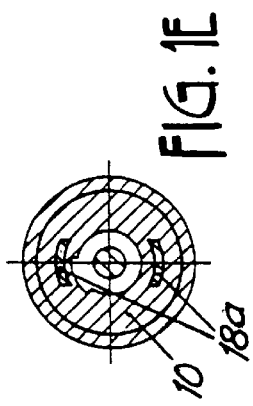
Figure 1D:
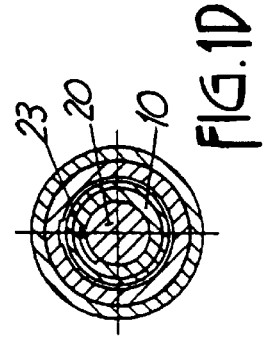
Figure 1E:
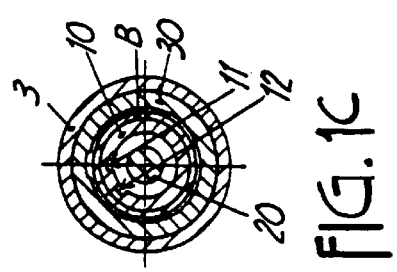
Figure 1F:
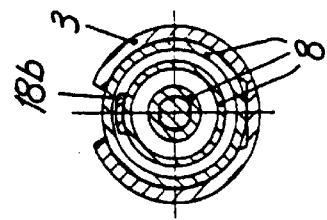
Figure 1G:
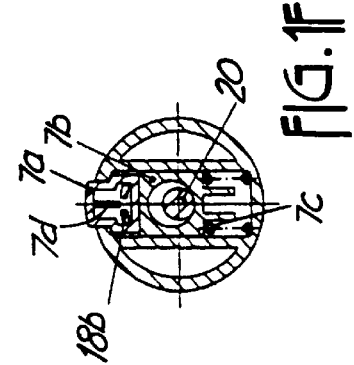
Figure 1H:
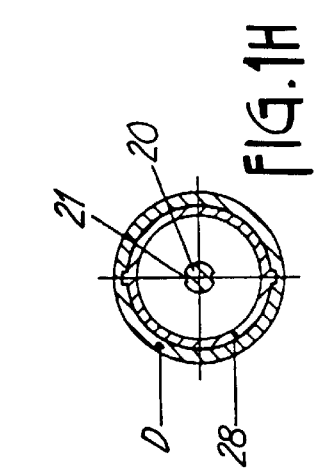
Figure 1I:
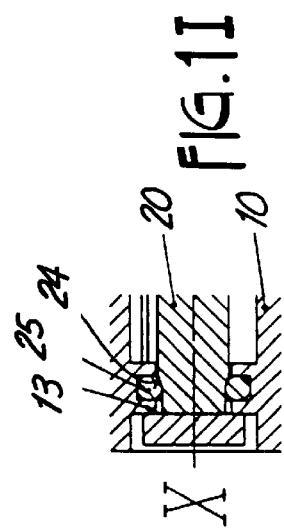

The accompanying Figures and this description depict and describe embodiments of the injection device and methods of the present invention, and features and components thereof. With regard to means for fastening, mounting, attaching or connecting the components of the present invention to form the device as a whole, unless specifically described otherwise, such means are intended to encompass conventional fasteners such as threaded connectors, snap rings, clamps such as screw clamps and the like, rivets, toggles, pins and the like. Components may also be connected by adhesives, glues, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or special orientation.

FIG. 1 include a longitudinal section and several cross sections showing an auto-injection device in accordance with the present invention, having the general shape of a pen and comprising an inserted container B, designed in the embodiment as a dual-chamber ampoule. The injection device is shown directly after insertion of the container B in an enclosure, which is formed essentially by a front sleeve-type enclosure 2 and a rear sleeve-type enclosure 3 joined thereto, for example by screw attachment. A front end of the front sleeve-type enclosure 2 is formed by a needle protector 1 attached to the front sleeve-type enclosure 2, said needle protector 1 being configured as a shell-type sleeve. At its rear face, the rear sleeve-type enclosure 3 is covered by a case cap 4.

When inserting the container B, the container B is pushed into a container bracket 30 up to a stop, accommodated in the front sleeve-type enclosure 2 and projecting from the same rearwardly prior to assembly of the device. The container bracket 30 is used for retaining and centering the container B. The container bracket 30 can be moved against the return force of a return element 31, for example a compression spring, in relation to the enclosure from its rear position shown in FIG. 1 to a forward position. Thereby the container B accommodated in the container bracket 30 is displaced together with the container bracket 30. This displacement is used for inserting a hypodermic needle N in the course of an auto-injection.

The container B is a circular cylinder widened at a side within the area of a front piston K1. An outlet of the container B at the front end, in the FIG. 1 the left-hand end of the container B, is closed by a diaphragm. Said diaphragm has been pierced by the hypodermic needle N prior to using the container B. Two in-line pistons K1 and K2 are displaceably accommodated in the container B. In the starting state, a powdered drug may be provided in a front chamber of the container, the left-hand chamber of the container in the FIG. 1, and a carrier liquid may be provided in a rear chamber of the container formed between the two pistons K1 and K2.

The injectable product, the drug solution, is formed by advancing the rear piston K2 against the front piston K1. Thereby the carrier liquid is displaced through the widened side section of the container wall into the front chamber. Thus the drug is dissolved in the carrier liquid. This condition is shown in FIG. 1.

The rear piston K2 is advanced when assembling the front sleeve-type enclosure 2 and the rear sleeve-type enclosure 3. For this purpose, a mixing member 10, formed as a sleeve body, is provided in the rear sleeve-type enclosure 3 secured against rotation. The mixing member 10 comprises a front sleeve portion with an external diameter smaller than the internal diameter of the container B and a rear sleeve portion widened in relation to said front sleeve portion. The transition between these two sleeve portions is designed as a shoulder 14, projecting radially from said front sleeve section. The shoulder 14 is formed circumferentially, but may also be formed by at least one radially projecting web. The rear end face of the mixing member 10 contacts webs 6, radially projecting inwards from the rear sleeve-type enclosure 3; said webs may also be designed as a circumferential wall. When assembling the device, i.e. whilst screwing the two sleeve-type enclosures 2 and 3 together, the mixing member 10, accommodated and secured against displacement in the rear sleeve-type enclosure 3, is introduced into the container B, which is open at the rear, and pushed forward in the same. As a result, the mixing member 10 pushes the rear piston K2 forward (in the direction toward the needle N) towards the front piston K1, until the rear piston K2 has reached the position shown in FIG. 1. In this position of the pistons K1 and K2, assembly of the sleeve-type enclosures 2 and 3 by screwing has been completed.

A drive unit is arranged in the rear sleeve-type enclosure 3, comprising a drive element 5 designed in this embodiment as a compression spring, and a rod-shaped driven member 20, guided straight into the enclosure. The drive element 5 is clamped between the webs 6 and a circumferential shoulder face of the driven member 20, said shoulder face facing the webs 6 oppositely in forward direction.

The driven member 20 is arranged around a central longitudinal axis of the enclosure, coinciding with its own central axis and allowing reciprocating rotation between two rotary positions. A metering sleeve D is provided as an extension of the enclosure for rotating the driven member 20. In its rear section projecting into the metering sleeve D, the driven member 20 comprises guide grooves 21, extending in advance or forward direction; a guide sleeve 28, projecting into the cover cap 4, firmly blocked against displacement and rotatable in relation to the said cap 4, and an indicator sleeve 8 arranged in the enclosure, firmly secured against displacement and rotatable, engage in said guide grooves 21. The guide sleeve 28 is connected to the metering sleeve D, firmly secured against rotation, as may be best seen in section H—H. The guide sleeve 28 is used for transferring the rotation of the metering sleeve D to the drive member 20. The indicator sleeve 8, connected to the driven member 20 firmly secured against rotation, is used for indicating the position of rotation of the driven member 20 and therefore for indicating the set metered amount. For this purpose the indicator sleeve 8 is provided with markings at its external circumference, in the shown embodiment with two markings for one each of the two rotary positions of the driven member 20. Said markings may be read through an opening in the enclosure. The indicator sleeve 8 and the guide sleeve 28, together with the mixing member 10, act as a straight guide for the driven member 20.

The driven member 20 is retained by a locking and release mechanism in its rear basic position shown. Said locking and release mechanism comprises a release means 7a, designed as a release button, acting on a locking means 7b transversely to the direction of displacement of the driven member 20. The structure and mode of operation of the locking and release mechanism is best shown in the joint view of the longitudinal section and cross section F—F.

The locking means 7b is formed by a sleeve comprising a passage through which the driven member 20 projects. For straight guidance, the locking means 7b is guided transversely to the advance/forward and longitudinal direction of the driven member 20 between two straight webs of the enclosure. The sleeve of the locking means 7b therefore comprises corresponding straight external faces, each facing said two webs of the enclosure. The passage of the locking means 7b is larger than the external diameter of the projecting driven member 20. When exerting pressure on the release means 7a, the locking means 7b is displaced against the force of a return element 7c formed by a compression spring transversely to the forward direction of the driven member 20. In the blocked position, the driven member 20 contacts a rear face of the locking means 7b by a shoulder 26 formed by a thickened section. This stop is released by transverse displacement of the locking means 7b. The driven member 20 is released from the locking means 7b and may be displaced in longitudinal direction under the engaging pressure of the drive member 5.

A safety device ensures that the release means 7a can only be actuated and therefore the driven member 20 can only be released when a container B has been inserted into the enclosure. Said safety device comprises a release locking body 18 and a compression spring 19. The release locking body 18 comprises a central sleeve section from which two webs 18a project forwardly in longitudinal direction (section E—E). Said two webs 18a project through two suitably formed slots in the shoulder 14 of the mixing member 10 and engage the rear edge of the container B. A third web 18b projects from the central sleeve section of the release locking element 18 towards the rear in longitudinal direction. Said third web 18b projects through the release means 7a, as best shown in the joint view of the longitudinal section and two cross sections F—F and G—G. At the height or level of the release means 7a, i.e. in the section projecting through the release means 7a, the third web 18b of the release locking body 18 comprises a longitudinal slot. A rib 7d of the release means 7a, radially projecting inwards, enters said longitudinal slot upon actuation of the release locking element 18, if the slot of the release locking body 18 is at the same height as the internal rib 7d of the release means 7a. As seen in longitudinal direction behind the slotted section the third web 18b of the release locking body 18 is again formed as a closed web. The compression spring is tensioned between the web 6 on the enclosure side and a shoulder projecting inwardly from the inner jacket face of the central sleeve section of the release locking body 18. Once a container B has been inserted, the two front webs 18a of the release locking body 18 push against the rear edge of the container B, thus being retained in the position shown in the longitudinal section of FIG. 1, allowing the internal rib 7d of the release means 7a to enter the slot of the release locking body 18, and to transversely displace the locking means 7b. Should a container not have been inserted, the release locking body 18 is pushed forwardly by the compression spring 19 into the annular gap, which is now free, until the central sleeve section of the release locking body 18 contacts the shoulder 14 of the mixing member 10. In this blocking position of the release locking body 18, the rear closed portion of the third web 18b of the release locking body 18 is positioned in front of the internal rib 7d of the release means 7a. Thus a transverse displacement of the release means 7a is no longer possible. The drive mechanism is now blocked.

A drive coupling exists between the mixing member 10 and the driven member 20, projecting through the driven member 20, allowing the mixing member 10 to be entrained by the driven member 20 upon an advance of the driven member 20, i.e. being advanced itself in relation to the enclosure. Said coupling is effected by a positive locking and a frictional connection in the front section of the mixing member 10. Said coupling is formed by a first coupling means 13, a second coupling means or inclined shoulder 24 and a third coupling means 25.

The first coupling means 13 is a front web of a guide groove for the third coupling means 25, said groove being formed between two peripheral webs at the internal jacket face of the mixing member 10. The third coupling means 25 is a ductile or flexible washer, in the embodiment a spring elastic washer, provided longitudinally with one slot like a piston ring. The second coupling means 24 is formed by a shoulder generated by widening of the rod-shaped driven member 20. When advancing, the driven member 20 pushes said second coupling means 24 against the third coupling means 25 and this in turn against the first coupling means 13, with the advance of the driven member 20 therefore also effecting the advance of the mixing member 10. Simultaneously, the mixing member 10 acts as a transfer member, transferring the forward movement of the driven member 20 to the container bracket 30 and the container B when its peripheral shoulder 14 pushes against the container bracket 30 and the container B. The shoulder 14 therefore acts as a drive for the container B.

Within an area provided in the container B, the mixing member 10 and the driven member 20 form the metering device of the present invention. For this purpose, the mixing member 10 is provided with a recess in the internal jacket section behind the first coupling means 13. Said recess comprises two grooves 11 and 12 extending in forward direction, arranged parallel to each other at offset angles. In forward direction, the said grooves 11 and 12 are of different lengths. The shorter groove 11 is formed as a dead groove in the jacket face and the longer groove 12 is limited in forward direction by the rear web of the seat for the third coupling means 25. At their rear ends, the grooves 11 and 12 end in a widened section of the recess at the same height in relation to forward direction, as best shown in the joint view of the longitudinal section and cross sections C—C, D—D and E—E. The widened section of the recess extends up to the rear end face of the front sleeve portion of the mixing member 10. The opposite facing sidewalls of the widened section ending at this point, are each extended by one of the grooves 11 and 12 in forward/advance direction.

The rod-shaped driven member 20 is provided with a cam 23, radially projecting outwardly. In the starting position of the injection device, the cam 23 engages the widened section of the recess of the mixing member 10. Said recess with the two grooves 11 and 12 forms a first metering means, and the cam 23 forms a second metering means of the metering device.

In a first metering position, the cam 23 is positioned flush to the groove 11 on the first sidewall of the widened section extending in forward direction, and in the second metering position, the cam 23 is positioned flush to the second sidewall of the widened section of the recess extending in forward direction. In the starting position, the driven member 20 is free to rotate in either direction around its longitudinal axis between said two metering positions. The two sidewalls of the wide groove define the two rotational and metering positions of the driven member 20, and the lengths of the two narrow grooves 11 and 12 define the amount of the drug solution to be dispensed during injection.

The widened section of the recess in the mixing member 10 could also be extended to the end of the short groove 11 in forward direction, with the recess assuming a simple stepped shape in forward direction.

For executing an auto-injection, the auto-injection device is positioned on a tissue surface, in particular human skin, with a front needle protector sleeve 9, which may be pushed back in relation to the enclosure and/or the front needle protector 1. When exerting pressure against the surface of the tissue, the needle protector sleeve 9 is pushed back to its rearmost position in relation to the enclosure. The hypodermic needle, firmly attached to an outlet at the front end of the container B in forward direction, is initially still surrounded by the needle protector 1, and the needle protector sleeve 9 is pushed over the same, up to and beyond its front tip, therefore not yet being in contact with the tissue surface.

For actuation, i.e. for inserting the needle and dispensing the drug solution, the user pushes the release means 7a inwardly in radial direction after having positioned the driven member 20 by means of the metering sleeve D into the required rotational and metering position. The locking means 7b is pushed away below the stop shoulder 26 by pushing inwardly, thus releasing the driven member. Subject to the pressure of the drive element 5, the driven member 20 and by means of the coupling also the mixing member 10 is advanced in relation to the enclosure. Positive locking and the frictional connection between the driven member 20 and the mixing member 10 is of sufficient strength to effect entrainment of the mixing member 10 pushing its shoulder 14 against the container bracket 30 and the container B, advancing the same in relation to the enclosure and against the return force of the return element 31 up to frontal position, defined by the enclosure-sided stop 32.

In the frontal position of the container bracket 30 or the container B, the coupling releases the drive connection between the driven member 20 and the mixing member 10.

Under the continued pressure of the drive element 5, the flexible washer 25 is compressed due to the mixing member 10 being fixed, thus being pushed over the second coupling means or inclined shoulder 24. The driven member 20 now advances further, also in relation to the mixing member 10, simultaneously also pushing the two pistons K1 and K2 forwardly in the container towards the container outlet. The drug solution is then dispensed through the needle inserted into the tissue whilst the container B is in its frontal position.

In the first metering position, the advance of the driven member 20 is limited by the front end of the groove 11. In the first metering position, dispensing is completed upon the cam 23 touching the wall of the groove extending in circumferential direction.

After retraction of the needle N, the injection device is prepared for a second injection. For this purpose, only the driven member 20 is to be initially retracted in relation to the mixing member 10 against the forward/advance direction. The front end of the driven member 20 comprises a stamp or ram 22, designed as a flange-type widened section. When dispensing the drug solution, the ram 22 of the driven member 20 pushes against the rear piston K2, and during retraction the rear circulating/peripheral shoulder face of the ram 22 pushes against the web 13 projecting from the internal jacket face of mixing member 10. During further retraction of the driven member 20 the mixing member 10 is thereby entrained, i.e. also pushed back up to its rear position, as shown in FIG. 1. The container bracket 30 and the container B accommodated therein follow the movement of the mixing member 10 due to the pressure of the return element 31. The return force of the return element 31 is relatively low in relation to the drive force of the drive element 5, thus not interfering whilst the container B is advanced for inserting the needle N.

For the next injection, the driven member 20 is rotated to its second metering position, in which the cam 23 is positioned flush with the groove 12. In this position, the driven member 20 may be advanced in relation to the mixing member 10 so far as to allow any residual quantity of the drug solution to be dispensed when actuating the drive mechanism, i.e. the release means 7. Forward movement is limited by a stop flange 27.

FIG. 2 shows an injection device comprising a metering device arranged within the container B, allowing four set dose amounts of a drug solution to be dispensed. The injection device is a simple injection device in the sense that the user inserts the needle manually and exerts continuous manual pressure to the metering button D of the driven member 20 for dispensing the solution.

In the embodiment of FIG. 2, the mixing member 10 fulfils both the function of mixing the drug solution and metering the amount of the drug solution to be dispensed. The following describes differences from the injection device of FIG. 1. Features and components in common in the embodiments are commonly referenced.

The container B is arranged in the front sleeve-type enclosure 2, secured against displacement. After screwing the two sleeve-type enclosures 2 and 3 together, i.e. after completing its mixing function, the mixing member 10 is also accommodated within the enclosure secured against displacement. It comprises, when looked at in forward direction of the driven member 20, a front sleeve portion, a central sleeve portion, widened in relation to the same and another widened rear sleeve section, sitting closely enveloping in the enclosure. The front sleeve section of the mixing member 10 acts as a slideway (or race-like guiding and support structure or travel path) for the driven member 20. The central sleeve section extends up to the internal walls of the container.

In the central sleeve section, the mixing member 10 comprises a stepped guide channel 17 on an internal jacket face. A rear channel section each, extending in forward direction, is connected by a subsequent channel section extending in circumferential direction to a channel section next frontal to it when looked at in forward direction, facing again in forward/advance direction. The guide channel 17 forms the first metering means. The second metering means 23 is again designed as a cam, projecting directly from an external jacket face of the driven member 20 and guided in the guide channel 17 upon advancing the driven member 20. Accidental erroneous metering is safely eliminated due to the course of the guide channel 17 with the two-sided guide system of the cam 23 when seen in forward direction. Rotation into the next metering position will only be possible upon the cam 23 having reached the end of a channel section extending in forward direction, i.e. after the set product dose of the previous metering position has been dispensed.

The metering position of the driven member 20 in relation to the enclosure may again be read through an opening in the enclosure from an indicator sleeve 8, which is attached to the metering button D and secured against rotation. The metering button D is mounted to the rear section of the driven member, projecting from the enclosure towards the rear. In its front section, it forms an annular gap around the driven member 20. A return element 29, acting as a pressure spring, has been provided in said annular gap and is supported opposite the shoulder section between the rear and the central sleeve section of the mixing member 10.

Figure 3:
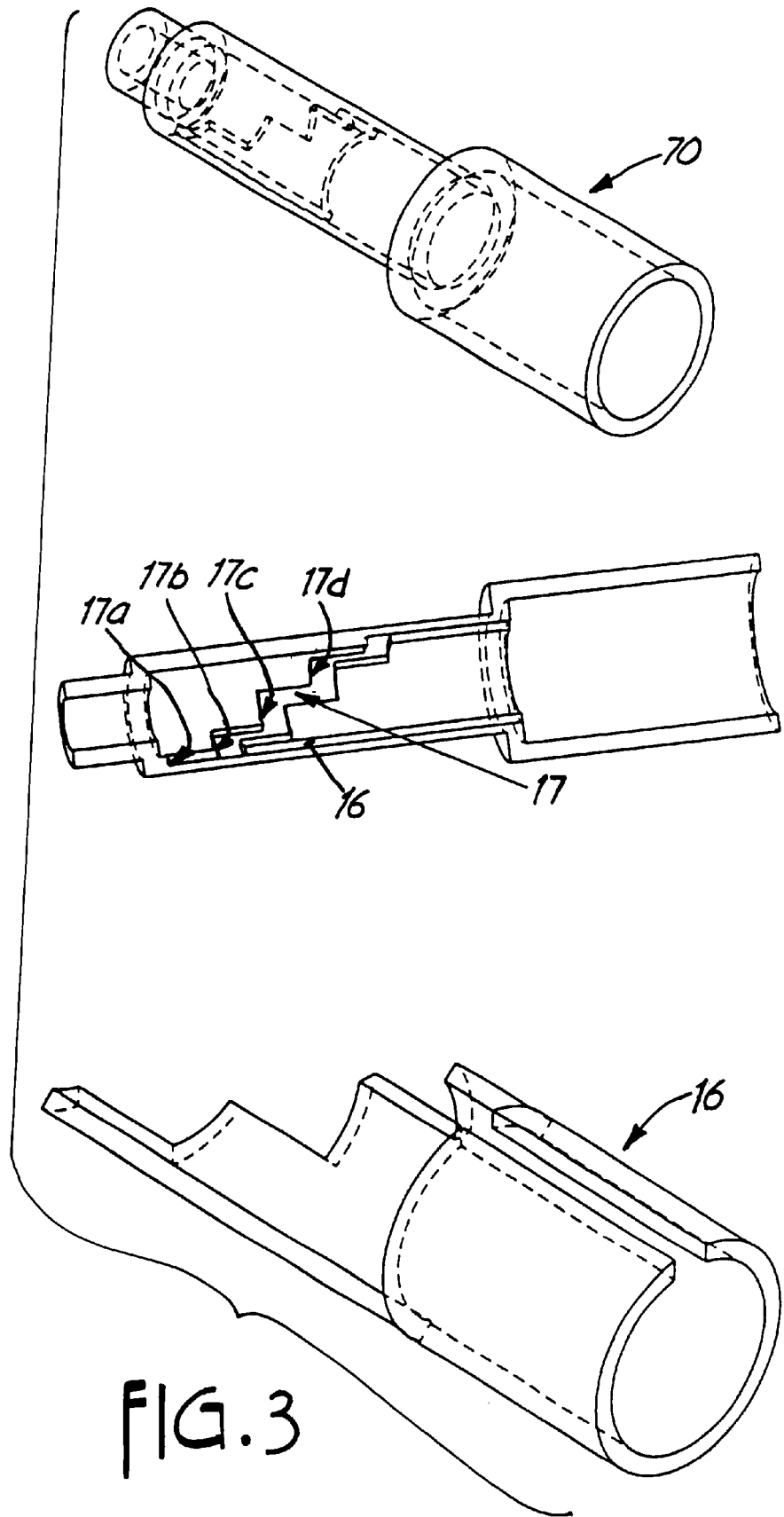
FIG. 3 depicts the transfer and metering means of the present invention in context of the injection device depicted in FIG. 2.

The mixing member 10 is separately and individually shown in FIG. 3. The first metering means, i.e. the guide channel 17 formed on the internal jacket area of the mixing member 10, is obtained by assembling several components. The central sleeve section of the mixing member 10 of the embodiment is a circular cylinder. An additional sleeve 16 is inserted in this sleeve section for forming the guide channel 17 and is suitably attached in its angular position. The central sleeve section of the mixing member 10 comprises a section raised inwardly, including a rear stepped face area. The additional sleeve 16 is of a contour following said stepped shape, by which it is pushed into the mixing member 10 spaced oppositely from the raised central sleeve section. The faces of the central sleeve section facing each other and of the sleeve body 16 form the sidewalls of the guide channel 17, thus forming stop faces 17a, 17b, 17c and 17d, facing against the forward direction. The heights of these stop faces 1a to 17d define the metered amounts when dispensing the drug solution. The raised section in the mixing member 10 may also be formed by a separate bowl- or sleeve-type body, also to be attached in the sleeve body of the mixing member 10, which would be smooth in this case.

The design of each of the first metering means may also be reversed, and the present invention may be embodied in other specific forms without departing from the essential spirit or attributes thereof. The described embodiments should be considered in all respects as illustrative, not restrictive.

What is claimed is:

1. A device for metered administration of an injectable product, comprising:

(a) a base section,
(b) a container arranged in said base section, from which container a dose of the injectable product is dispensed through a needle by advancing in a forward direction at least one piston arranged in said container,
(c) a drive unit comprising a driven member projecting into the container, said driven member advancing the piston in said forward direction upon actuation of the drive unit, and
(d) a metering device for choosing a length over which the driven member is displaced in relation to the base section, said metering device comprising a first metering mechanism and a second metering mechanism, the second metering mechanism being adjustable in relation to the first metering mechanism, wherein the first and second metering mechanisms are arranged in said container and metering is effected by interaction of the first and the second metering mechanisms within said container, and wherein said first metering mechanism is formed by a recess in a cylindrical jacket surface, wherein said recess comprises two side walls extending in said forward direction, and a connection of these side walls comprising a wall section extending in circumferential direction and against said forward direction, said wall section serving as stop for said second metering mechanism.

2. A device for metered administration of an injectable product, comprising:

(a) a base section,
(b) a container arranged in said base section, from which container a dose of the injectable product is dispensed through a needle by advancing in a forward direction at least one piston arranged in said container,
(c) a drive unit comprising a driven member projecting into the container, said driven member advancing the piston in said forward direction upon actuation of the drive unit, and
(d) a metering device for choosing a length over which the driven member is displaced in relation to the base section, said metering device comprising a first metering means and a second metering means, the second metering means being adjustable in relation to the first metering means, wherein the first and second metering means are arranged in said container and metering is effected by interaction of the first and the second metering means within said container, wherein said first metering means acts as a guide channel for said second metering means, and wherein said guide channel is provided by joining together two cylindrical bodies, wherein at least one of these bodies is a sleeve body having an end face forming a side wall of said guide channel.

3. A device for metered administration of an injectable product, comprising:

(a) a base section.
(b) a container arranged in said base section, from which container a dose of the injectable product is dispensed through a needle, wherein said container is a multi-chamber ampoule comprising at least two chambers arranged generally axially with respect to the ampoule one behind the other, said chambers being separated from each other by a frontal piston and being closed by a rear piston, said rear piston being displaced towards said frontal piston when the contents of the two chambers are mixed by means of a mixing member projecting into said container, said mixing member being forwardly displaceable in said container, (c) a drive unit comprising a driven member projecting into the container, said driven member advancing the piston in said forward direction upon actuation of the drive unit, and (d) a metering device for choosing a length over which the driven member is displaced in relation to the base section, said metering device comprising a first metering means and a second metering means, the second metering means being adjustable in relation to the first metering means, wherein the first and second metering means are arranged in said container and metering is effected by interaction of the first and the second metering means within said container, wherein said first metering means comprises said mixing member.

4. A device for metered administration of an injectable product, comprising:

(a) a base section, (b) a container arranged in said base section, from which container a dose of the injectable product is dispensed through a needle by advancing in a forward direction at least one piston arranged in said container, (c) a drive unit comprising a driven member projecting into the container, said driven member advancing the piston in said forward direction upon actuation of the drive unit, and (d) a metering device for setting a length over which the driven member is displaced in relation to the base section, said metering device comprising a first metering means and a second metering means, the second metering means being adjustable in relation to the first metering means, wherein the first and second metering means are arranged in said container and metering is effected by interaction of the first and the second metering means within said container, wherein the device is an auto-injection device and further wherein said container is advanced in relation to said base section by said driven member in order to insert a needle carried by the container.

5. The device as set forth in claim 4, characterized in that a component of the metering device comprising said first metering means, serves as a transfer member, transferring a forward movement of said driven member to the container, until said container has reached a forward position in relation to said base section.

6. The device as set forth in claim 1, wherein said second metering mechanism is directly connected to said driven member.

7. The device as set forth in claim 1, wherein the device is an auto-injection device and further wherein said container is advanced in relation to said base section by said driven member in order to insert a needle carried by the container.

8. The device as set forth in claim 7, wherein a component of the metering device comprising said first metering mechanism, serves as a transfer member, transferring a forward movement of said driven member to the container, until said container has reached a forward position in relation to said base section.

9. The device as set forth in claim 2, wherein said second metering means contacts a stop during advancement of said driven member, thus limiting the length of the displacement of the driven member.

10. The device as set forth in claim 2, wherein said second metering means is directly connected to said driven member.

11. The device as set forth in claim 2, wherein the device is an auto-injection device and further wherein said container is advanced in relation to said base section by said driven member in order to insert a needle carried by the container.

12. The device as set forth in claim 11, wherein a component of the metering device comprising said first metering means, serves as a transfer member, transferring a forward movement of said driven member to the container, until said container has reached a forward position in relation to said base section.

13. The device as set forth in claim 3, wherein said second metering means contacts a stop during advancement of said driven member, thus limiting the length of the displacement of the driven member.

14. The device as set forth in claim 3, wherein said second metering means is directly connected to said driven member.

15. The device as set forth in claim 3, wherein the device is an auto-injection device and further wherein said container is advanced in relation to said base section by said driven member in order to insert a needle carried by the container.

16. The device as set forth in claim 15, wherein a component of the metering device comprising said first metering means, serves as a transfer member, transferring a forward movement of said driven member to the container, until said container has reached a forward position in relation to said base section.

* * * * *

UNITED STATES PATENT AND TRADEMARK OFFICE
CERTIFICATE OF CORRECTION

| | |
|---|---|
| PATENT NO. | : 6,290,679 B1 |
| DATED | : September 18, 2001 |
| INVENTOR(S) | : Peter Hostettler and Hanspeter Heiniger |

It is certified that error appears in the above-identified patent and that said Letters Patent is hereby corrected as shown below:

Column 1,
Line 6, please delete "19821934.3" and insert -- 19821934.2 -- therefor.

Column 3,
Line 51, please delete "special" and insert -- spacial -- therefor.

Column 4,
Line 14, please delete "in the FIG. 1" and insert -- in FIG. 1 -- therefor.
Line 21, please delete "in the FIG. 1" and insert -- in FIG. 1 -- therefor.

Signed and Sealed this

Fifth Day of March, 2002

*Attest:*

JAMES E. ROGAN
*Director of the United States Patent and Trademark Office*

*Attesting Officer*